United States Patent
Goldstein et al.

(10) Patent No.: US 12,268,874 B2
(45) Date of Patent: Apr. 8, 2025

(54) VARIABLE ELECTROSTIMULATIVE BEHAVIOR MODIFICATION

(71) Applicant: Intellishot Holdings Inc., Delray Beach, FL (US)

(72) Inventors: Steven Wayne Goldstein, Delray Beach, FL (US); Michael Edward Smith Luna, Broadmoor Village, CA (US)

(73) Assignee: Intellishot Holdings Inc., Delray Beach, FL (US)

( * ) Notice: Subject to any disclaimer, the term of this patent is extended or adjusted under 35 U.S.C. 154(b) by 0 days.

(21) Appl. No.: 18/128,462

(22) Filed: Mar. 30, 2023

(65) Prior Publication Data

US 2023/0233854 A1   Jul. 27, 2023

Related U.S. Application Data

(63) Continuation of application No. 17/151,555, filed on Jan. 18, 2021, now Pat. No. 11,642,521.
(Continued)

(51) Int. Cl.
*A61N 1/05* (2006.01)
*A61B 5/0533* (2021.01)
(Continued)

(52) U.S. Cl.
CPC ........ *A61N 1/36028* (2013.01); *A61B 5/0533* (2013.01); *A61N 1/0456* (2013.01);
(Continued)

(58) Field of Classification Search
CPC .............. A61N 1/36028; A61N 1/0456; A61N 1/0476; A61N 1/36031; A61N 1/36034; A61N 1/18; A61N 1/0529; A61B 5/0533; A61B 5/117; G06F 3/041; G06F 2203/04101; G07C 9/00563
See application file for complete search history.

(56) References Cited

U.S. PATENT DOCUMENTS 5,916,087 A   6/1999   Owens
9,119,539 B1  9/2015   Dotan et al.
(Continued)

*Primary Examiner* — Michael J Lau
*Assistant Examiner* — Anh-Khoa N Dinh
(74) *Attorney, Agent, or Firm* — HEA Law PLLC; Darrin A. Auito

(57) ABSTRACT

A method for variable electrostimulative behavior modification includes sensing placement of a first anatomical portion of a body in contact to a surface of a target object adapted for behavior modification with a multiplicity of electrostimulative end points coupled to an energy source. The method additionally includes delivering an electrical neurostimulus through one of the end points nearest to the placement of the first anatomical portion in proximity to the surface the electrical neurostimulus including a waveform promoting a modification of behavior associated with the placement of the first anatomical portion in proximity to the surface. Thereafter, an anomalous characteristic of the sensed placement indicating a failure to modify the behavior may be detected and a profile of the waveform of the electrical neurostimulus changes to a different waveform in response to the anomalous characteristic of the sensed placement.

24 Claims, 2 Drawing Sheets

Related U.S. Application Data

(60) Provisional application No. 62/963,110, filed on Jan. 19, 2020, provisional application No. 62/963,107, filed on Jan. 19, 2020.

(51) Int. Cl.
  *A61N 1/04* (2006.01)
  *A61N 1/36* (2006.01)
  *G06F 3/041* (2006.01)
  *G07C 9/00* (2020.01)

(52) U.S. Cl.
  CPC ....... *A61N 1/0476* (2013.01); *A61N 1/36031* (2017.08); *A61N 1/36034* (2017.08); *G06F 3/041* (2013.01); *G07C 9/00563* (2013.01); *G06F 2203/04101* (2013.01)

(56) References Cited

U.S. PATENT DOCUMENTS

| | | | |
|---|---|---|---|
| 9,480,846 | B2 | 11/2016 | Strother et al. |
| 10,002,474 | B1 | 6/2018 | Fernandez |
| 10,629,058 | B1 | 4/2020 | Nengelken |
| 11,100,737 | B1 * | 8/2021 | Goldstein ............... G06F 3/041 |
| 2003/0074039 | A1 * | 4/2003 | Puskas .................. A61N 1/056 607/118 |
| 2003/0163709 | A1 | 8/2003 | Milgramm et al. |
| 2003/0214418 | A1 | 11/2003 | Hahne et al. |
| 2005/0285747 | A1 | 12/2005 | Kozlay |
| 2006/0049938 | A1 | 3/2006 | Wilson |
| 2006/0055534 | A1 | 3/2006 | Fergusson |
| 2006/0248341 | A1 | 11/2006 | Lambert et al. |
| 2010/0031139 | A1 | 2/2010 | Ihara |
| 2010/0304874 | A1 | 12/2010 | Abatemarco |
| 2011/0102137 | A1 | 5/2011 | Schroeter et al. |
| 2012/0222667 | A1 | 9/2012 | Vendramini et al. |
| 2012/0298119 | A1 | 11/2012 | Reese et al. |
| 2013/0244724 | A1 | 9/2013 | Monti et al. |
| 2015/0254948 | A1 | 9/2015 | Acosta et al. |
| 2016/0175589 | A1 * | 6/2016 | Wingeier ............ A61B 5/4836 607/45 |
| 2018/0122167 | A1 | 5/2018 | Maggioni |
| 2018/0349589 | A1 | 12/2018 | Perna et al. |
| 2019/0278897 | A1 | 9/2019 | Zhang et al. |
| 2019/0282152 | A1 * | 9/2019 | Ouwerkerk ............ A61B 5/681 |
| 2020/0003511 | A1 | 1/2020 | Deng et al. |
| 2020/0035052 | A1 | 1/2020 | Arnold |
| 2021/0020008 | A1 | 1/2021 | Deutsch |
| 2021/0213286 | A1 * | 7/2021 | Covalin ............ A61N 1/36036 |

\* cited by examiner

VARIABLE ELECTROSTIMULATIVE BEHAVIOR MODIFICATION

REFERENCES TO THE RELATED PATENT APPLICATION

The present application claims priority to and is a continuation application of pending U.S. application Ser. No. 17/151,555, filed on Jan. 18, 2021, which claims benefit of U.S. Provisional Application Nos. 62/963,107 and 62/963,110, both filed on Jan. 19, 2020. The content of the above documents is incorporated herein by reference in its entirety.

TECHNICAL FIELD

The present disclosure relates to the field of electrified objects and more particularly the use of neural stimuli to modify mammalian behavior.

BACKGROUND

Behavior modification refers to modification of behavior of a mammal including a human being. Behavior change (or modification) may be realized in different forms, for example it may be used to aide in the formation of new habits or repeated behaviors (either avoided or induced), alternatively behavior change may be simply for guidance into or away for an action, activity or such at a moment in time. In this way the concept of behavior change is inclusive of habit cessation, habit formation, or action guidance.

Positive reinforcement is a technique for promoting behavior modification. Yet, every subject varies for whom behavior modification is sought and the context of the required behavior modification varies from circumstance to circumstance such that in some instances, positive reinforcement is more likely to evoke a desired modification to behavior, whereas for another subject, perhaps a minimal application of negative reinforcement is required, whereas in yet other instances, a maximal application of negative reinforcement is required, but in all circumstances, the correct selection of positive or negative reinforcement and the magnitude, e.g. the size of such reinforcement must account for the well-being of the target subject which must remain of paramount importance.

SUMMARY

Embodiments of the present disclosure address deficiencies of the art with respect to behavior modification and provide a novel and non-obvious method, system and computer program product for variable neurostimulative excitation to elicit behavior modification. The science of neurostimulation may include auditory, optical, electrical, olfactory, gustatory, alone or in any combination thereof. One aspect of the present disclosure focuses on electrical neurostimulation, but it is known that the techniques taught herein may be applied to one or more types of neurostimulation, alone or in combination. The combination of neurostimulation can be delivered in serial or parallel.

The applications of this concept for behavior modification are far reaching, for example, the behavior modification system taught herein could be applied in the applications described below.

First, in a law enforcement scenario, for example, it may adjust the neurostimulation wavesform response based on the resistance of a detained subject. For example, the stimulation may be incorporated into a pair of shackles, hand-cuffs, issued clothing, law enforcement vehicles (e.g. barriers and cages), which sense, through motion passive or aggressive behavior and deliver the appropriate type of neurostimulation to correct, guide or change the behavior of the detainee. Furthermore, the neurostimulation response can be triggered from users or a group of users, such that in a prison, if the prisoners were motivated to have an uprising, any prisoner wearing a pair of shackles, hand-cuffs, issued clothing, law enforcement vehicles (e.g. barriers and cages), and who would be in proximity to the neurostimulation would also be affected to modify their behavior.

Second, in an application of theft or unwanted physical movement or motion of a target object, for example, the neurostimulation may change its variable neurostimulus wavesforms response current (amperes) and compliance voltage based on proximity or distance to a location, home station, charging station, room, door or other demarcation point.

Another application, for example, is controlling access to food. In this regard, it is well known that intermittent fasting can help one lose weight, improve health and perhaps even live longer. But restraining oneself from accessing food at a particular time of the day or for an extended period is very challenging. One method of enabling compliance, is to include an electronic barrier to deter the user attempting to gain access to an area or container containing the food, either through variable neurostimulative or in combination with other deterrents such as acoustic and or optical.

The present disclosure is not limited to the above three examples. For example, the method, system and computer program described herein may apply to many other markets or domains such as animal control, crowd control, home or building security, teaching, learning to play music, enhancing the movement of a golf swing, improving running, detouring access to controlled substances etc.

According to one embodiment of the present disclosure, a method for variable electrostimulative behavior modification includes a learning system with a sensing placement of a first anatomical portion of a body of a target subject in proximity to a surface of an object that has been adapted to induce behavior modification with a multiplicity of electrostimulative end points coupled to an energy source. An energy source is a source of stored or controlled energy which is then delivered to the electrostimulative end points as a combination of waveshape, current (amperes) and compliance voltage.

Note that the terms waveshape and waveform are herein used to signify, encompass, and describe all aspects of a time varying stimulus. This includes, but is not limited to: the shape of the wave pulse (such as but not limited to sinusoidal, square, triangle, sawtooth); intensity changes to the signal during a single pulse, including but not limited to attack or rise time, decay, sustain, or release time; the amplitude of the wave; the duration of one period or pulse of the wave (this is also known as the pulse width); the duration of any period of non-signal between pulses; the number of pulses; the temporal attributes of a series of pulses, including but not limited to the frequency of pulses; ratio of "on" versus "off" portions of the stimulus (also known as duty cycle); overall duration of stimulus presentation; and any other simple or complex attributes of a periodic stimulus. Thus, changing the waveform may, for example, involve lengthening the pulse width while, for example, maintaining the pulse repetition frequency, which would result in increasing the duty cycle. Any combination of changes to any set of attributes may result in different stimuli; as indicated, any or all of these changes are herein referred to as changes to the waveform or waveshape.

The method may include delivering an electrical neurostimulus, which can be delivered to induce a pleasant sensation (positive reinforcement) or an unpleasant sensation (negative reinforcement) through the electrostimulative end points closest to the sensed proximity so as to provide a desired electrostimulative sensation upon the target subject. Thereafter, an anomalous characteristic of the sensed placement may be detected and learned by the system, the anomalous characteristic indicating an inadequacy of the delivered electrical neurostimulus in achieving the desired behavior modification as otherwise had been expected in consequence of the delivery of the electrical neurostimulus. In response, a profile of the waveform of the electrical neurostimulus changes to produce a different, electrical neurostimulus to the target subject is either enhanced or decreased. In this way, the minimal positive or negative reinforcement is applied to the target subject initially, but a more intensive reinforcement signal may subsequently be applied to the extent that it is determined the more intensive reinforcement is required in order to promote the desired behavior modification or conversely a less intensive reinforcement signal may be subsequently applied to the extent that it is determined a less intensive reinforcement is required to promote the desired behavior modification This ensures the absolute non-adverse health risk given the limit on current and duration of current delivery coupled with the counterbalancing delivery of energy, and the absolute safest delivery of neurostimulus to the target subject while still eliciting the intended behavior modification.

According to one aspect of this embodiment, a threshold measurement is derived at a location of the placement of the first anatomical portion the surface of the object, for instance a force applied by the placement of the anatomical portion, the orientation of the placement of the anatomical or physical portion, or a duration of time during which the anatomical or physical portion remains proximate to the location. Alternatively, another characteristic, a threshold measurement of moisture of the first anatomical portion.

According to another aspect of this embodiment, a separately sensed proximity between a second anatomical portion of the body of the target subject and a location of the surface of the object is determined.

Alternatively, another characteristic, a threshold measurement of galvanic skin response (e.g., a change in the electrical resistance of the skin caused by emotional stress, measurable with a sensitive galvanometer, such as in lie-detector tests) of the first anatomical portion is used to sense the location, resistance of the sensed location and the waveform of neurostimulus to be delivered.

According to another aspect of this embodiment, the electrical neurostimulus can be delivered without the user making physical or direct contact with a pair of electrodes. Once the proximity of the user has been detected, the electrical neurostimulus signal can be propagated using a high voltage discharge system capable of crossing a spark gap enabled by a Tesla coil. Tesla coils can produce output voltages from 50 Kilovolts of volts. The alternating current output is in the range typically between 50 kHz and 1 MHz.

According to another aspect of this embodiment, the changed profile is a change in frequency of the electrical neurostimulus. Alternatively, the changed profile is a change in the amplitude of the electrical neurostimulus. As yet a further alternative, the changed profile is a change in the waveform of the electrical neurostimulus. As yet a further alternative, the changed profile is a change in current or it may be a change in energy. In fact, any combination of the foregoing may also account for the changed profile.

The primary motivating feature of the electrical neurostimulus is the delivery of electrical charge (e.g., current) from the electrostimulative surface to the anatomical portion of the subject of behavioral modification. The appropriate unit of measure of delivered charge (e.g., current) is Amperes (or milliAmperes, mA). The voltage of the electrical stimulation will need to be sufficient to enable the transit of electrical charge, and will need to vary in order to maintain a constant current. As indicated in Ohms law, voltage=current*resistance. Consider, for example, a desired behavioral experience (or perhaps a maximum safe current) occurs with the delivery of a current of 5 mA or 0.005 A. In the case of bare human skin contacting an electrostimulative surface, the impedance to the electrical stimulus presented by said human skin varies between approximately 2,000 and 50,000 Ohms (though this varies considerably, depending on skin hydration, oils, location on the body, and the presence of calluses, etc.). The exact momentary impedance of an anatomical portion also varies with current, and with time, thus it is imperative to specify the delivery of charge in term of constant current, and consequently to continually modify the voltage of the signal in order to compensate for momentary variations in the total impedance of the anatomical portion, the coupling or contact with the surface, and other environmental variables. In the example case of bare human skin contacting an electrostimulative surface, the voltage will typically need to vary from 10 V to 200 V to keep the current constant at the prescribed 5 mA. Typically, a system with a maximum, or "compliance," voltage of approximately 100 or 200 Volts is sufficient to support the flow of charge necessary for behavior modification in this circumstance.

A system intended to deliver a constant current (amperage) needs to adjust the voltage (up to the compliance voltage), over the course of the anatomical portion's contact with the surface. The voltage may also need to be adjusted to compensate for different intervening dielectric materials between the anatomical portion and the surface of the electrode. For example, a much higher voltage may be required if there is any electrical obstruction, such as oil, dirt, or even the material of a glove, between the anatomical portion and the electrostimulative surface. Higher voltages (even as high as 75,000 V) could be used to deliver current through insulators like oil or gloves, particularly when coupled with higher-frequency (e.g., 200 kHz) stimuli.

The system may include an authentication electronics for determining whether the user is authorized for access to the object or space and countermeasure disabling electronics for disabling countermeasure electronics, such as energy source configured to deliver electrical neurostimulus to at least one of a plurality of electrostimulus end points on the object, when the user is authenticated for access to the object or space.

According to one embodiment, the authentication electronics can be incorporated in the sensor configured to detect placement of a first anatomical portion of a body in proximity to a surface of the object. The authentication electronics can also include a biometric interface used to authenticate the user and provide access to the object or space without delivering an electrical neurostimulus to the user. The biometric interface can take the form of voice recognition, facial recognition, iris recognition, fingerprint recognition, ear print recognition, gait and cadence recognition, ECG ID recognition, or other forms of biometric identifiers including subcutaneous identifiers known as vein detection.

The authentication electronics may communicate with an authentication engine that may be part of a controller for the system. The authentication may be configured to acquire and store information, e.g., palm print, fingerprint and geometry, every time a user attempts to gain access to the object. Thus, the system is configured to preserve authorized and non-authorized user attempts. During setup or other, the system learns the authorized users vein patterns, hand geometry, etc.

In use, the system, for example, can transmit all actions encountered by the authentication engine, such that an administrator of the system can receive live time coded information (e.g., video feeds, pictures, etc.). The information can be preserved locally or in the cloud, for forensic applications.

According to another embodiment, a data processing system is adapted for variable electrostimulation to induce behavior modification. The system includes an object, a power source, an energy source, a sensor operatively coupled to the object and sensing placement of a first anatomical portion of a body or anatomical portion of a target subject in proximity to a surface of the object and a multiplicity of electrostimulative end points coupled to the power source and affixed to the surface of the object. The system further includes a controller coupled to the sensor and end points. The controller includes a processor, memory and computer program instructions stored in the memory. In one embodiment the instructions are enabled upon execution by the processor to deliver electrical neurostimulus through one of the end points nearest to a location of the sensed placement, detect a characteristic of the sensed placement, and respond to the characteristic by changing a profile of the electrical neurostimulus.

According to one aspect of this embodiment, the instructions learn an optimal profile over time for each target subject by first identifying the subject, either biometrically or by external identification means such as but not limited to identification badge, by way of image recognition, feature detection, voice recognition, iris recognition, chemical analysis, DNA analysis, motion analysis, weight and height, gait analysis, and the like. Thereafter, the nature of the change in profile of the electrical neurostimulus applied to the target subject is recorded in connection with the target subject. Subsequently, upon identifying the target subject, the same change in the profile of the electrical neurostimulus may be applied to the target subject at the outset upon sensing the placement in order to ensure that repeatable and consistent behaviors are performed to achieve the desired behavioral modification outcome.

According to another aspect of this embodiment, the instructions are enabled to discontinue the delivery of the electrical neurostimulus through one of the end points subsequent to determining a removal of the first anatomical portion from the proximity of the surface.

According to another embodiment, the profile may determine the leading direction of the simulation, either anodic or cathodic, in order to create a distal or proximal sensation relative to the target endpoint. These directional sensations can be used to provide guidance for the user. In one example, the neurostimulus is embedded into the wearable device which is used for a enhancing a golf swing. The user is presented with neurostimulus to specific locations across their anatomy as well as anodic to cathodic or cathodic to anodic to produce directional cues for the users of the wearable. This information can be shared with others remotely to monitor conditioning and to measure improvement in the swing.

Additional aspects will be set forth in part in the description which follows, and in part may be derived from the description, or may be learned by practice. The aspects will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The following drawings illustrate examples of various components of embodiments of the disclosure described herein and are for illustrative purposes only. Embodiments of the present disclosure are illustrated by way of example and not limitation in the figures of the accompanying drawings, and in which.

DETAILED DESCRIPTION

Figure 1:
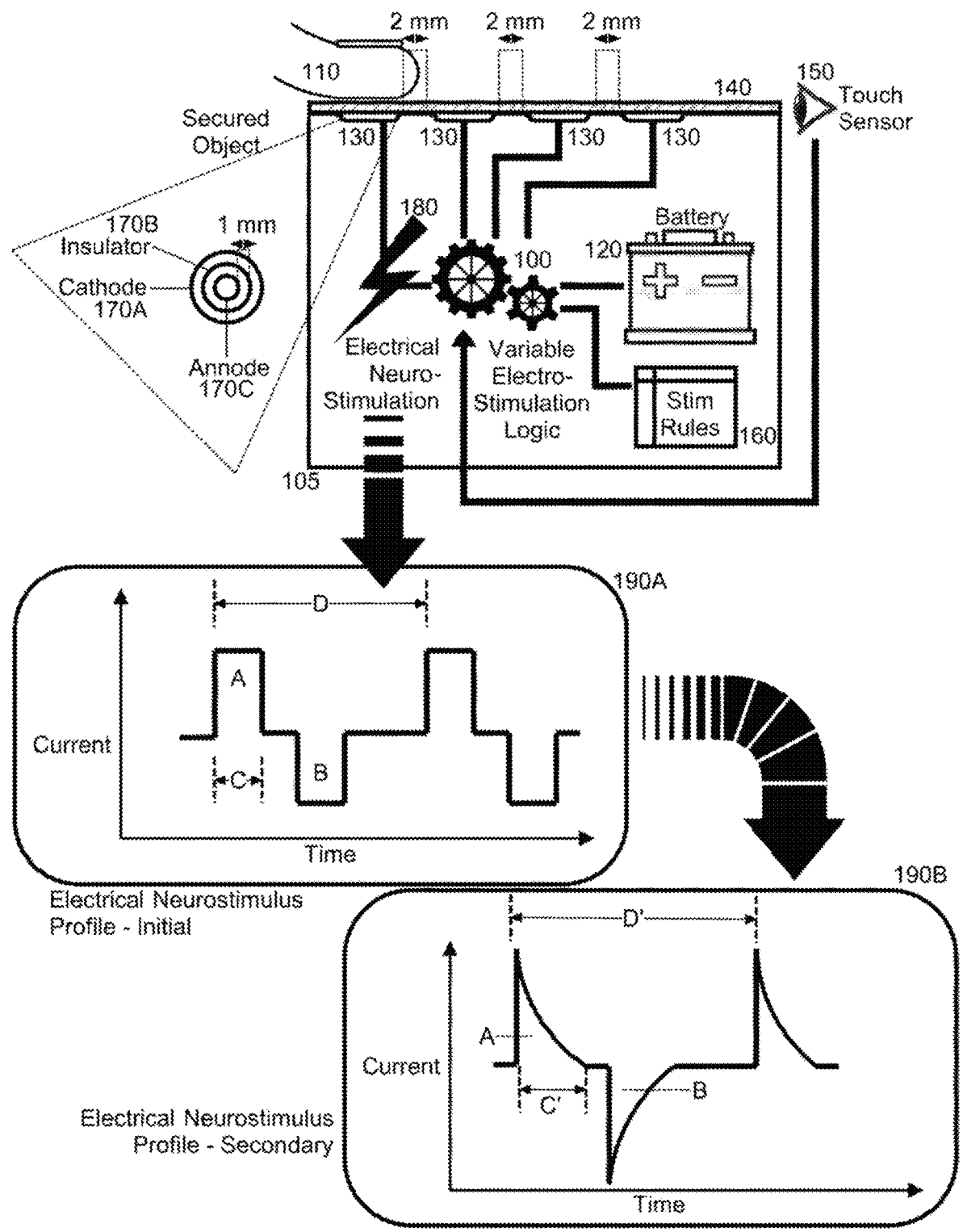
FIG. 1 illustrates a process for variable electrostimulative behavior modification, according to one embodiment.

Embodiments of the disclosure are described that provide for variable electrostimulative behavior modification. In accordance with one embodiment of the disclosure, a proximity of a portion of the anatomy of a target subject is sensed in connection with a surface of a target object. The sensing of the proximity of the anatomical portion may be accomplished by several means including, but not limited to, ultrasonic, optical, acoustical, image recognition, biometric, radiofrequency, magnetic, chemical, altimeter, thermal, humidity, light, SPL (level) keyword, inductive, capacitive, resistive, inertial measurement unit, movement, rotation, force (for example by means of a strain gauge) or the sensing of current flowing in the system. Upon sensing the proximity of an anatomical portion with the surface, a location on the surface proximate to the anatomical portion is determined. Then, an electrical neurostimulus is generated in accordance with an initial waveform profile of specific current, energy, amplitude and frequency, and delivered to an electrode end point at the location or other location prescribed.

In one aspect of the embodiment, a sensing system is configured to determine the direction and speed of the approaching of the target subject. These data points can be used to determine the overall intent of the target subject intentions. An image recognition system can be added to identify and verify the target subjects' identity. Using the subject intentions, the system will generate an electrostimulative signal delivered by direct contact or by non-direct contact in response to the subject's intentions, identity or a combination of both. The enhancement of the predictive threat analysis and waveform generation from such will be optimized.

In one aspect of the embodiment, the neurostimulus continues to be delivered through the electrode end point until such time as the proximity is no longer sensed. However, during the delivery of the neurostimulus, if a characteristic of the proximity is detected such as a threshold duration of time during which the proximity is maintained, a threshold impedance measured at the location, a threshold resistance measured at the location, a threshold capacitance measured at the location, a threshold force applied by the anatomical portion at the location, a threshold measurement of moisture of the anatomical portion, or the placement of a second anatomical portion of the anatomy in proximity to a different location upon the surface, then the neurostimulus is generated in conformance with a different waveform and delivered near the anatomical portion or to a set of defined end points not in the proximity of the sensed are so as to intensify or reduce the neurostimulation in an attempt to discourage or encourage the target subject from continuing to maintain the anatomical portion in proximity to the target object or otherwise guide the subject's actions and direction based of the waveform.

Examples of guidance provided to a target user includes directing a user in or out of a room, or directing a user to move away from an object or to return towards a position from which the user had previously traveled. Another example can include a change in a golf swing, baseball swing, or a tennis swing.

Another example can include the playing of specific keys on a musical instrument like a piano while not playing other specific keys of the musical instrument. In respect to the latter example, an electrostimulus is applied to a key selected not to be played so that if the key is played, or attempted to be played, the end user may be discouraged from doing so.

FIG. 1 illustrates one embodiment of a process for variable electrostimulative behavior modification. As shown in FIG. 1, an array of electrostimulative end points 130 are placed on or in a surface 140 of target object 105, e.g., container, input device, door knob or handle, handcuffs, a safe or vault, or any other type of target object. Each of the electrostimulative end points 130 can be separated from one another by a distance determined by a combination of the dielectric breakdown voltage of the substrate material, the average dielectric breaks down voltage of air, the operating compliance voltage and the target charge density to ensure the desired effect of the stimulus waveform. In no cases are the end points to be placed so closely together such that dielectric breakdown occurs between them, and the spacing between the electrostimulative end points 130 may differ for some of the electrostimulative end points 130. In one aspect of the embodiment the spacing is no less than 2 mm which ensures that upon contacting a portion of the anatomy 110, the current of a delivered electrical neurostimulus 180 cannot flow so deeply into the anatomy of the target subject so as to activate unwanted structures such as motor nerves. Other spacing parameters could be utilized that do not depart from this design objective.

The electrostimulative endpoints 130 can include cathode 170A and anode 170C separated by an insulator 170B by at least one millimeter (1.0 mm). In one embodiment, the 1.0 mm separation of anode 170C from cathode 170A ensures that an electric field created in the portion of the anatomy 110 proximate to an associated pair of the electrostimulative end points 130 will be deep enough into the portion of the anatomy so as to effectively stimulate mechanoreceptors typically laying 1.0 mm to 3.0 mm from the skin surface while avoiding stimulating smaller nociceptors that lay superficial to the mechanoreceptors. Other separation parameters could be utilized that do not depart from this design objective.

In another aspect of the embodiment, the compliance voltage is adjusted as to deliver the electrical neurostimulus 180 by ensuring that the distance of breakdown occurs at the desired proximity distance and the average dielectric breakdown voltage of air (or glove material or clothing). This may include adjustment of the compliance voltage by measuring real-time environmental conditions such as current weather, humidity, temperature, gas levels, alone or in combination. Known measuring techniques can be utilized. This provides a means to deliver the desired stimulation waveform without necessitating physical skin contact with the end point that is adjusted to match the possible intervening environmental conditions.

As shown in FIG. 1, battery 120 (as an energy source) powers each of the pairs of electrostimulative end points 130 in so far as variable electrostimulation logic 100 is adapted to generate an electrical neurostimulus 180 of alternating current (AC) having a specific profile in terms of voltage, current, energy, frequency and shape, and to selectively deliver the current or energy of the generated electrical neurostimulus 180 to the electrostimulative end points 130. In one aspect of the embodiment, the electrical neurostimulus 180 includes a current of no greater than one-hundred milliamperes (100 mA) for a period of energy delivery of no greater than one and one-half seconds (1.5 s) so as to provide for a maximum energy delivery of one-half Joule but should not exceed five Joules for humans, but can vary based on the type and mass of mammalian. The apparatus (system) and method disclosed considers increasing the overall level of Joules required for the specific use case such as electrical fence used to contain animal(s). The level of energy required to safely modify the behavior of a cow, a bull, a horse, etc. would cause fatality to a human.

In one embodiment for human application, the electrical neurostimulus 180 is a 5 mA signal of two-tenths seconds (0.2 s) duration providing for twenty-five (25) pulses per second may serve as the maximum waveform that would be delivered. Other parameters could be utilized that do not depart from this design objective. Other energy sources, such as AC power may be used in addition to or instead of as a battery to power the eletrostimulative end points 130.

Such a system could be implemented in numerous ways. For example, a high voltage generator circuit including, for example, LT 3420 Photoflash Capacitor Charger with Automatic Refresh or similar.

In one aspect of the embodiment, touch sensor 150 is disposed upon the surface 140 of the target object 105. The touch sensor 150 is configured to detect a proximity or contact to the surface 140 of the portion of the anatomy 110 of the target subject, such as a fingertip of a finger of a human hand, a digit of a mammal, a paw, a toe, a foot, a leg, an arm, a neck, an appendage, an entire hand or other anatomical regions of interest. Contrary to its naming convention, the touch sensor 150 does not require direct contact, e.g., with an anatomical region. A touch sensor 150 can detect movement of the anatomical region. In this regard, the touch sensor 150 can be a capacitive touch screen, or an optical touch screen, as well as ultrasonic, optical, acoustical, image recognition, biometric, RF, magnetic, chemical, altimeter, thermal, humidity, light, SPL (level) keyword, inductive, capacitive, resistive, inertial measurement unit, force (for example by means of a strain gauge) or the sensing of current flowing in the system or from human oversight, all adapted to detect a proximity or contact of a touch upon the surface 140 and to locate upon the surface 140 a position of the proximity or contact location. Finally, variable electrostimulation logic 100 responds to the touch sensor 150 by selectively controlling delivery of the electrical neurostimulus 180 to the electrostimulative end points 130 closest to the location reported by the touch sensor 150 or to an adjacent and specific predefined area.

Of note, the variable electrostimulation logic 100 responds to an anomalous characteristic of the proximity of the touch by changing a profile 190A of the electrical neurostimulus 180 to a different profile 190B. Optionally, the variable electrostimulation logic 100 responds to a determination by the touch sensor 150 that no further proximity to the surface 140 remains by discontinuing (or delivering for positive sensation) delivery of the electrical neurostimulus 180 to the one of the electrostimulative end points 130.

This can be accomplished, for example, by using a galvanic skin response amplifier circuit, skin impedance amplifier circuit, or other similar means or combinations thereof. This type of monitoring or detection can be used for various embodiments discussed herein.

As another option, upon detecting by the touch sensor 150 multiple different portions of the anatomy 110 coming into proximity or contact with the surface 140, subsequent to the detection by the touch sensor 150 of the initial proximity or contact to the surface 140 of the portion of the anatomy 110 of the target subject, the delivery of the electrical neurostimulus 180 is disabled at all electrostimulative end points 130.

When the touch sensor 150 senses an initial proximity to the surface 140 of the target object 105 at a specified location of the portion of the anatomy 110 of the target subject, the variable electrostimulation logic 100 selects an initial waveform profile 190A for the electrical neurostimulus 180. The initial waveform profile 190A may be fixed or, in the alternative, variably selectable according to rules 160, each of the rules 160 correlating a particular characteristic of the proximate contact with a particular waveform profile, or based on previously saved, or learned and adapted profile. For example, the rules could be previously defined and stored in a lookup table. Each waveform profile defines a current, amplitude, duration energy, period/duty-cycle, and shape of the electrical neurostimulus 180, such as sine wave, square wave, saw tooth wave, H-wave, a positive or a negative going wave etc, a frequency of the electrical neurostimulus 180 and an amplitude of the electrical neurostimulus 180. In the example of an H-wave waveform as shown in FIG. 1, a positive delivery of energy A for duration C is provided in concert with a negative delivery of energy B of equal but opposite magnitude for an equal duration C so that the combination accounts for a period D.

The variable electrostimulation logic 100, however, changes the profile 190A to a different profile 190B upon detecting an anomalous characteristic of the proximate contacting of the surface 140. Such anomalous characteristics include, for instance, a threshold duration for which the contacting persists, a threshold force by which the contacting occurs, a threshold impedance measured at the location of contacting (indicative of the presence of a skin barrier such as a glove), a particular location of the contacting upon the surface 140, or the detection of a separate contacting of the surface 140 at a different location while the contacting at the initial location of the surface 140 remains. The different profile 190B may be selected according to the rules 160 and may each include any combination of a different shape of the electrical neurostimulus 180, a different amplitude of the waveform, or a different frequency determined by a different period D' of a combination of the delivery of positive energy A' for duration C' counterbalanced by the delivery of negative energy B' also for the duration C'.

In consequence of the foregoing arrangement, the behavior of the individual directly contacting or by being in close proximity to the target object 105 may be modified. Specifically, while the electrical neurostimulus 180 of the first profile 190A may provide a pleasant or unpleasant sensation, such as a sensation of pain or discomfort, through a mild electrostimulative experience, the anomaly causing the change to the second profile 190B may provide a more intense pleasant or unpleasant electrostimulative experience through an extended duration D' of energy delivery, a greater frequency at which the energy is delivered or a greater amplitude of current delivered, in particular where the anomaly indicates an additional proximity by the individual, or where the anomaly indicates a prolonged period during which the proximity persists. As well, to the extent that the anomaly indicates the presence of an insulative layer such as a glove, or excessive moisture thereby inhibiting the intended effect of the electrical neurostimulus 180, the second profile 190B is enabled to overcome the insulative layer so as to achieve the desired behavior modification.

The foregoing arrangement is designed to achieve electrostimulative behavior modification without risking unintended, adverse health risk given the limit on current and duration of current delivery coupled with the counterbalancing delivery of energy within the AC electrical neurostimulus 180.

To illustrate examples of how the waveform and/or other attributes of an electrical neurostimulus may be changed in a systematic manner, to modify behavior, consider the stimulus parameters listed in Table 1, below. These values are illustrative, and actual deployed values would potentially depend on the exact formation and implementation of the electrostimulative surface; the contour and shape of the surface; the specific portion of anatomy (e.g., finger versus palm of the hand versus paw); and the contact, coupling, or area of the portion of the anatomy that is in contact with the surface. The example parameters from Table 1 could be generated by a system with compliance voltage of, for example, 200 Volts, with actual momentary voltages ranging from approximately 10-200 Volts, depending on the specifics of what anatomical portion is in contact with the surface, the nature of the skin, the area of contact, and so on.

In one embodiment, a design decision is made for the target subject to be aware that the surface they are touching is conducive in some fashion, and may lead the target subject to take action to remove them finger or other anatomical unit from the surface they are in contact with.

A Pulse Repetition Rate of 30 Hz has been found to elicit a psychological response as a warning before the user experiences a tingle or any pain. If the Pulse Repetition Rate is in the range of 30 Hz, the sensation the user experiences is that of a constant sensation, without the benefit of an imbedded warning signalizing characteristic.

TABLE 1

Example Adjustable Electrostimulus Parameters (Square Wave Pulse).

| Pulse Maximum Amplitude/Current [milliAmp] | Pulse Duration (pulse width) [millisecond] | Pulse Repetition Rate [Hertz] | Example Reported Sensation (one finger in contact) |
|---|---|---|---|
| 5.0 | 0.20 | 30 | "tingle" |
| 5.0 | 1.00 | 30 | "buzz" |
| 5.0 | 2.00 | 30 | "light zap" |
| 5.0 | 3.00 | 30 | "strong zap"/"painful" |
| 5.0 | 4.00 | 30 | "moderately painful" |
| 5.0 | 5.00 | 30 | "extremely painful" |

Considering the example parameters in Table 1, an example implementation might include enabling an initial electrostimulation profile that elicits a "tingle" sensation when one human finger contacts the electrostimulative surface (pulse duration of 0.20 mS, as depicted in Table 1). If the required behavior is to remove the finger from the surface, and if that behavior is not detected (i.e., the subject persists in touching the surface), then the profile of the stimulus may be modified, resulting in a more aversive stimulus being delivered via the surface (e.g., in this illustration, increasing pulse duration to 2.00 mS, yielding the more aversive sensation of a "light zap"). If the finger is removed, the behavioral change requirement will have been satisfied, and the stimulus profile may be returned to the initial/baseline profile (pulse duration 0.20 mS, which in this illustration would elicit the perception of a "tingle" if the initial or any other finger were to contact the electrostimulative surface again). If, however, the finger were not removed, or not removed within the timing parameters established in the behavior modification rule, then the profile of the electrostimulation could, for example, be modified again to be more aversive (e.g., pulse duration of 4.00 mS, or "moderately painful", in this illustration). Likewise, the profile and waveform of the electrostimulus may be modified to result in a particular behavior modification.

Further, the modification of the profile of the electrostimulus may proceed in either a more or less aversive direction, depending on the behavior modification requirements. The example of causing a subject to remove a finger (described previously) required a progressively more aversive electrostimulation. Other behaviors may require a progressively less aversive stimulation.

And further, the specific profile or profiles employed may depend on the nature of the subject, the anatomical portion, the detailed behavioral modification required, and the overall circumstances, among other things.

As one example, when designing an electrostimulative behavior modification system that has the goal of causing an individual to refrain from opening a cookie jar may require somewhat "gentle" parameters; whereas a system intended to cause a person to refrain from opening a storage box containing dangerous items may, by virtue of the likely subjects, or the importance of eliciting that behavior due to the dangerousness of the items, for example, may require more aversive electrostimuli.

And further, the specific profiles that are used in a sequence to modify behavior may depend on the same variety of situational variables. For example, the profiles used in a cookie jar, for example, might elicit a "tingle" then a "buzz" then a "light zap"; whereas deterring access to more dangerous items may require a "buzz" immediately followed by an "extremely painful" electrostimulation if the behavior still needs to be modified.

Figure 2:
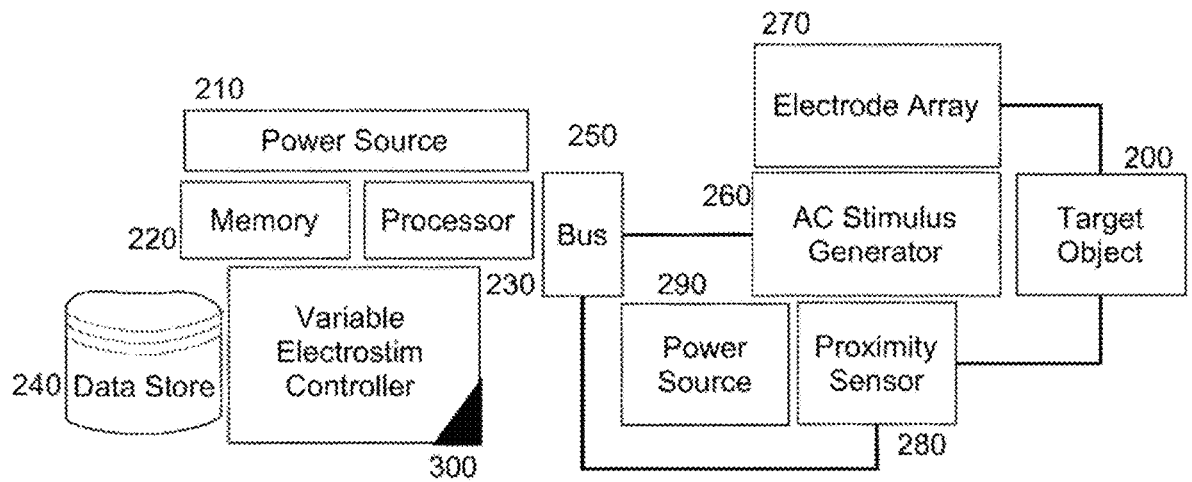
FIG. 2 illustrates a schematic of a data processing system adapted for variable electrostimulative behavior modification, according to one embodiment.

The process described in connection with FIG. 1 may be implemented within a data processing system. In further illustration, FIG. 2 schematically shows a data processing system adapted for variable electrostimulative behavior modification with respect to a target (secured) object 200, according to one embodiment. The system includes a host computing system that includes a power source 210 powering memory 220 and at least one processor 230 along with a persistent data store 240. The processor 230 is communicatively coupled both to proximity sensor 280 and AC stimulus generator 260 by way of communications bus 250. Both the proximity sensor 280 and the AC stimulus generator 260 are powered by power source 290. The proximity sensor 280 is directly coupled to the secured object 200. The AC stimulus generator 260 is coupled to an array of electrode endpoints including at least one pair or a multiplicity of anode-cathode pairs, disposed on or within a surface of the target object 200. Optionally, each of the anode-cathode pairs is of a rounded shape to avoid sharp corners likely to concentrate current during the delivery of an electrical neurostimulus, and protrudes from the surface of the target object 200 so as to provide for the delivery of robust electrical neurostimulus to a proximate portion of the anatomy.

In one embodiment, when using a high-voltage system (KEV), the cathode and anode electrode placement can be modified whereas one of the electrodes is connected to the ground plane as the other electrode will cross the spark gap and deliver the electrostimulus through the air.

The system includes a variable electrostimulative controller 300 executed by the processor 230 in the memory 220. The controller 300 includes computer program instructions that, during execution by the processor, are enabled to receive from the proximity sensor 280, an indication of threshold proximity of an anatomical portion of the anatomy of a mammal including a human being, such as a digit, to the surface of the target object 200. In this regard, the threshold proximity can be a touching of the surface of the target object 200, a close presence of the anatomical portion to the surface, e.g. almost or nearly touching. In response to the indication of threshold proximity, the program instructions are configured to direct the AC stimulus generator 260 to generate an electrical neurostimulus of particular profile and to deliver the electrical neurostimulus to a specific end point in the end-point array 270 nearest to a location of the threshold proximity.

The program instructions yet further are enabled to detect an anomalous condition in respect to the threshold proximity of the anatomical portion, for instance a long duration of the threshold proximity, a measured impedance at the location of the threshold proximity, a measured pressure at the location of the threshold proximity, or a detection of an additional anatomical portion of the anatomy at a different location on the surface of the target object 200. As such, the program instructions are enabled to respond to the detection of the anomalous condition by locating in a table in the data store 240, an associated profile for an electrical neurostimulus and to direct the AC stimulus generator 260 to generate the electrical neurostimulus in accordance with the associated profile in place of the electrical neurostimulus of the particular profile presented in response to the initial detection of the threshold proximity.

Figure 3:
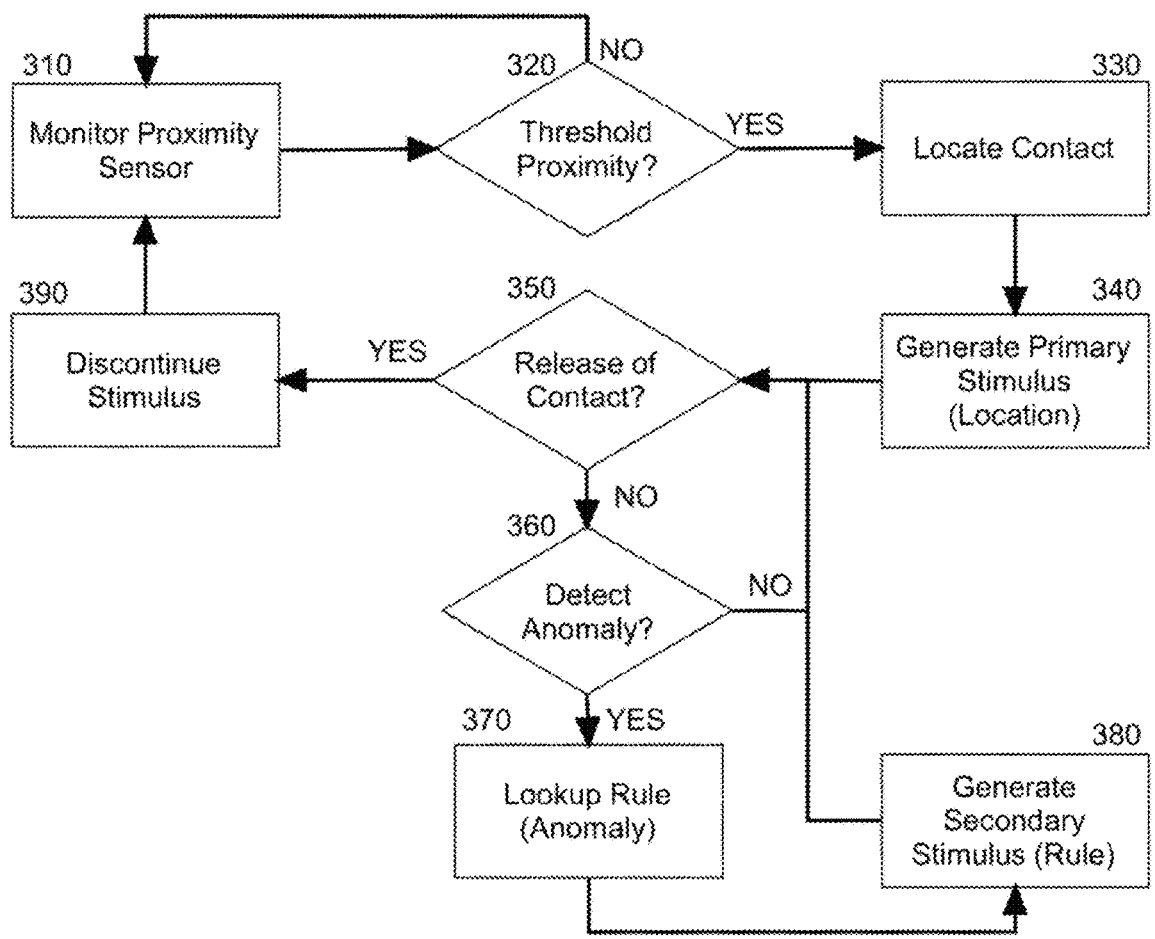
FIG. 3 illustrates a flow chart showing a process for variable electrostimulative behavior modification, according to one embodiment.

In even yet further illustration of the operation of the variable electrostimulative controller 300, FIG. 3 illustrates a flow chart illustrating a process for variable electrostimulative behavior modification, according to one embodiment. Beginning in block 310, the controller monitors the output of a proximity sensor and in decision block 320, it is determined whether a threshold proximity of a surface of the target object has occurred. For example, the proximity sensor may sense a touching or near touching of the surface, or a threshold movement of the surface, to name two possibilities. If not, then the controller continues to monitor the output of the proximity sensor. In decision block 320, upon detecting a threshold proximity, in block 330, a location of the threshold touching upon the surface of the target object is sensed and in block 340, a primary electrical neurostimulus is generated according to a first waveform profile including a particular shape, frequency and amplitude, and the electrical neurostimulus is delivered to a specific end points; a larger set of endpoints, a generalized area of multiple endpoints or multiple locations which form a larger array of neurostimulus endpoints on the surface of the target object nearest the sensed threshold proximity.

Optionally, in decision block 350, it is determined whether the threshold of proximity persists. If not, then in block 390 the controller discontinues delivery of the electrical neurostimulus at the determined location and the process returns to a state of monitoring the proximity sensor in block 310. If it is determined at decision block 350 that the threshold touching persists, then in decision block 360 it is further determined whether an anomalous condition exists as to the threshold touching. If yes, then in block 370 an electrical neurostimulus generation rule is matched to the determined anomalous condition and in block 380, a secondary electrical neurostimulus is generated according to new waveform profile implicated by the matched rule so that the secondary electrical neurostimulus has a profile that is different from the primary electrical neurostimulus. Thereafter, the process returns to decision block 350.

The present disclosure may be embodied within a system, a method, a computer program product or any combination thereof. The computer program product may include a computer readable storage medium or media having computer readable program instructions thereon for causing a processor to carry out aspects of the present disclosure. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing.

Computer readable program instructions described herein can be downloaded to respective computing/processing devices from a computer readable storage medium or to an external computer or external storage device via a network. The computer readable program instructions may execute entirely on the user's computer, partly on the user's computer, as a stand-alone software package, partly on the user's computer and partly on a remote computer or entirely on the remote computer or server.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special-purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer readable program instructions may also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present disclosure. In this regard, each block in the flowchart or block diagrams may represent a module, segment, or portion of instructions, which includes one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Finally, the terminology used herein is for the purpose of describing particular embodiments only and is not intended to be limiting of the disclosure. As used herein, the singular forms "a", "an" and "the" are intended to include the plural forms as well, unless the context clearly indicates otherwise. Furthermore, the terms "includes" and/or "including," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form described. Many modifications and variations will be apparent to those of ordinary skill in the art without departing from the scope and spirit of the disclosure. The embodiment was chosen and described in order to explain the principles of the disclosure and the practical application, and to enable others of ordinary skill in the art to understand the disclosure for various embodiments with various modifications as are suited to the particular use contemplated.

Although this disclosure has been described in connection with specific forms and embodiments thereof, it will be appreciated that various modifications other than those discussed above may be resorted to without departing from the spirit or scope of the disclosure as defined in the claims. For example, functionally equivalent elements may be substituted for those specifically shown and described, certain features may be used independently of other features, and in certain cases, particular locations of the elements may be reversed or interposed, all without departing from the spirit or scope of the disclosure as defined in the claims.

We claim:

1. A data processing system adapted for variable electrostimulative behavior modification, the system comprising:

an object;
an energy source;
a power source coupled to the energy source;
a sensor in communication with the object, the sensor configured to detect placement of a first anatomical portion of a body in proximity to a surface of the object;
a plurality of electrostimulative end points coupled to the energy source and the surface of the object; and
a controller connected to the sensor and the plurality of electrostimulative end points, the controller comprising a processor, memory, authentication engine in communication with the authentication electronics, and computer program instructions stored in the memory, the controller configured to:
receive data from the sensor, the data including the detected placement of the first anatomical portion of the body in proximity to the surface of the object,
determine whether the first anatomical portion of the body is authorized to access the object,
disable the energy source when the first anatomical portion of the body is authorized for access to the object,
instruct the energy source to deliver, based on the received data, a first electrical neurostimulus to at least one of the plurality of electrostimulative end points, wherein the first electrical neurostimulus is defined by a first waveform, when the first anatomical portion of the body is not authorized for access to the object;
determine, based on the received data, presence of an anomalous characteristic; and,
based on the determination of the presence of the anomalous characteristic, instruct the energy source to deliver a second electrical neurostimulus to at least the one electrostimulative end point, wherein the second electrical neurostimulus is defined by a second waveform, and the second waveform is different from the first waveform.

2. The data processing system adapted for variable electrostimulative behavior modification according to claim 1, wherein the at least one of the plurality of electrostimulative end points is an electrostimulative end point nearest the detected placement of the first anatomical portion in proximity to the surface of the object.

3. The data processing system adapted for variable electrostimulative behavior modification according to claim 1, wherein a profile of the second waveform produces an enhanced electrical neurostimulus relative to the electrical neurostimulus produced by the first waveform.

4. The data processing system adapted for variable electrostimulative behavior modification according to claim 1, wherein the second electrical neurostimulus is delivered for a predetermined period.

5. The data processing system adapted for variable electrostimulative behavior modification according to claim 1, wherein the anomalous characteristic indicates an inadequacy of the delivered first electrical neurostimulus in achieving a desired behavior modification.

6. The data processing system adapted for variable electrostimulative behavior modification according to claim 1, wherein the second waveform is configured to increase or decrease the delivered electrical neurostimulus defined by the first waveform.

7. The data processing system adapted for variable electrostimulative behavior modification according to claim 1, wherein
the energy source is a source of stored or controlled energy delivered to the electrostimulative end points as a combination of waveform, current and compliance voltage.

8. The data processing system adapted for variable electrostimulative behavior modification according to claim 1, wherein the system is configured to discontinue the delivery of the electrical neurostimulus through one of the end points subsequent to determining removal of the first anatomical portion from the proximity of the surface.

9. The data processing system adapted for variable electrostimulative behavior modification according to claim 1, wherein the controller is configured to instruct the energy source to deliver a third electrical neurostimulus to at least the one electrostimulative end point, wherein the third electrical neurostimulus is defined by a third waveform, and the third waveform is different from the first and second waveform.

10. The data processing system adapted for variable electrostimulative behavior modification according to claim 1, wherein
the sensor is a touch sensor disposed on the surface of the object,
the touch sensor is configured to detect a proximity or contact to the surface of the portion of the anatomy of the target subject, and
the touch sensor does not require direct contact with the anatomy of the target subject.

11. The data processing system adapted for variable electrostimulative behavior modification according to claim 1, wherein the sensor is configured to detect a galvanic skin response of the first anatomical portion to determine location, resistance, and waveform of the first electrical neurostimulus to be delivered.

12. The data processing system adapted for variable electrostimulative behavior modification according to claim 1, wherein
the controller is configured to instruct the electrical source to deliver the first electrical neurostimulus to the at least one of the plurality of electrostimulative end points without the first anatomical portion making direct contact with the object, and
the first electrical neurostimulus is propagated using a high voltage discharge system.

13. The data processing system adapted for variable electrostimulative behavior modification according to claim 1, wherein the authentication electronics is incorporated into the sensor.

14. The data processing system adapted for variable electrostimulative behavior modification according to claim 1, wherein each of the plurality of electrostimulative end points is separated from one another by a distance determined by a combination of dielectric breakdown voltage of the substrate material, average dielectric breakdown voltage of air, operating compliance voltage and target charge density to ensure the desired effect of the stimulus waveform.

15. The data processing system adapted for variable electrostimulative behavior modification according to claim 1, wherein each of the plurality of electrostimulative end points is separated from one another by at least 2.0 mm.

16. The data processing system adapted for variable electrostimulative behavior modification according to claim 1, wherein each of the plurality of electrostimulative end points is separated from one another by a distance preventing flow of the first electrical neurostimulus so deeply into the first anatomical portion so as to activate undesired biological structures, wherein the distance is at least 2 mm.

17. The data processing system adapted for variable electrostimulative behavior modification according to claim 1, wherein each of the plurality of electrostimulative end points includes a cathode and anode separated by an insulator by at least 1.0 mm.

18. The data processing system adapted for variable electrostimulative behavior modification according to claim 1, wherein each of the plurality of electrostimulative end points includes a cathode and anode separated by an insulator by a distance that generates an electrical current that stimulates mechanoreceptors laying 1.0 mm to 3.0 mm from the first anatomical portion while avoiding stimulating smaller nociceptors that lay superficial to the mechanoreceptors.

19. The data processing system adapted for variable electrostimulative behavior modification according to claim 1, wherein the controller is configured to measure realtime environmental conditions and instruct the energy source to deliver the first electrical neurostimulus based on the measured realtime environmental conditions.

20. The data processing system adapted for variable electrostimulative behavior modification according to claim 1, wherein the maximum waveform delivered is 5 mA signal of 0.2 seconds duration and 25 pulses per second.

21. The data processing system adapted for variable electrostimulative behavior modification according to claim 1, wherein the authentication electronics comprises a biometric interface configured for voice recognition, facial recognition, iris recognition, fingerprint recognition, ear print recognition, gait and cadence recognition, ECG ID recognition, or vein detection recognition.

22. The data processing system adapted for variable electrostimulative behavior modification according to claim 21, wherein the system is configured to store data received from the authentication electronics, including authorized and non-authorized user attempts.

23. The data processing system adapted for variable electrostimulative behavior modification according to claim 21, wherein the system learns an optimal profile of the electrical neurostimulus over time for each target subject by identifying the subject through the authentication electronics and recording, in connection with the target subject, the electrical neurostimulus delivered to the subject.

24. The data processing system adapted for variable electrostimulative behavior modification according to claim 23, wherein, upon identifying the target subject, the system is further configured to apply a recorded profile of the electrical neurostimulus to the target subject, wherein the recorded profile is the electrical neurostimulus previously delivered to the target subject that resulted in the discontinuing of the delivery of the electrical neurostimulus to the target subject.

* * * * *